United States Patent
Jinkerson

(10) Patent No.: US 8,043,607 B2
(45) Date of Patent: Oct. 25, 2011

(54) UV-ABSORBERS FOR OPHTHALMIC LENS MATERIALS

(75) Inventor: David L. Jinkerson, Benbrook, TX (US)

(73) Assignee: Novartis AG, Basel (CH)

(*) Notice: Subject to any disclaimer, the term of this patent is extended or adjusted under 35 U.S.C. 154(b) by 220 days.

(21) Appl. No.: 12/500,896

(22) Filed: Jul. 10, 2009

(65) Prior Publication Data

US 2010/0012889 A1     Jan. 21, 2010

Related U.S. Application Data

(60) Provisional application No. 61/080,864, filed on Jul. 15, 2008.

(51) Int. Cl.
- A61K 31/74 (2006.01)
- C07D 249/04 (2006.01)
- C07D 249/16 (2006.01)
- C07D 403/00 (2006.01)
- G02C 7/02 (2006.01)
- C09K 3/00 (2006.01)

(52) U.S. Cl. ............ 424/78.04; 548/255; 548/257; 548/260; 548/261; 514/912; 351/159; 252/183.11

(58) Field of Classification Search .......... 424/78.04; 548/255, 257, 260, 261; 514/912; 351/159; 252/183.11

See application file for complete search history.

(56) References Cited

U.S. PATENT DOCUMENTS

| | | | |
|---|---|---|---|
| 4,716,234 A | 12/1987 | Dunks et al. |
| 4,803,254 A | 2/1989 | Dunks et al. |
| 5,290,892 A | 3/1994 | Namdaran et al. |
| 5,331,073 A | 7/1994 | Weinschenk, III et al. |
| 5,470,932 A | 11/1995 | Jinkerson |
| 5,543,504 A | 8/1996 | Jinkerson |
| 5,637,726 A | 6/1997 | Collins et al. |
| 5,693,095 A | 12/1997 | Freeman et al. |
| 6,166,218 A | 12/2000 | Ravichandran et al. |
| 6,528,602 B1 | 3/2003 | Freeman et al. |
| 6,806,337 B2 | 10/2004 | Schlueter et al. |
| 6,846,897 B2 | 1/2005 | Salamone et al. |
| 6,852,793 B2 | 2/2005 | Salamone et al. |
| 6,872,793 B1 | 3/2005 | Schlueter et al. |
| 7,037,954 B2 | 5/2006 | Baba et al. |
| 7,067,602 B2 | 6/2006 | Benz et al. |
| 7,101,949 B2 | 9/2006 | Salamone et al. |
| 7,326,423 B2 | 2/2008 | Pearson et al. |
| 2006/0252850 A1 | 11/2006 | Jani et al. |
| 2007/0092830 A1 | 4/2007 | Lai et al. |
| 2007/0092831 A1 | 4/2007 | Lai et al. |
| 2008/0242818 A1 | 10/2008 | Benz et al. |
| 2008/0266519 A1 | 10/2008 | Schlueter |
| 2009/0043007 A1 | 2/2009 | Weinschenk, III et al. |
| 2009/0043105 A1 | 2/2009 | Weinschenk, III et al. |

FOREIGN PATENT DOCUMENTS

| | | | |
|---|---|---|---|
| CN | 1727338 | | 2/2006 |
| EP | 1033590 | | 7/2008 |
| FR | 2487831 | * | 2/1982 |
| FR | 2487832 | * | 2/1982 |
| JP | 2009013148 | | 1/2009 |
| JP | 2005053058 | | 7/2009 |
| WO | WO2008109624 A2 | | 9/2008 |

OTHER PUBLICATIONS

Takakis, et al., "Preparation of Benzofuroxans and Benzofurazans of 2,3,4,5-Tetrahydrobenzo[b][1.4]dioxocin and Related Compounds," J. Heterocyclic Chem., 1990, pp. 177-181, vol. 27.

Ricker, Jochen, et al., "Ultraviolet Stabilizers of the 2-(Hydroxyphenyl)benzotriazole Class. Influence of Substituents on Structure and Spectra," J. Phys. Chem. 1992, pp. 10225-10234, vol. 96.

* cited by examiner

*Primary Examiner* — Lorna M Douyon
*Assistant Examiner* — Tanisha Diggs
(74) *Attorney, Agent, or Firm* — Patrick M. Ryan

(57) ABSTRACT

Dihydroxybenzotriazole UV absorbing compounds that are particularly useful in ophthalmic devices are disclosed.

14 Claims, 1 Drawing Sheet

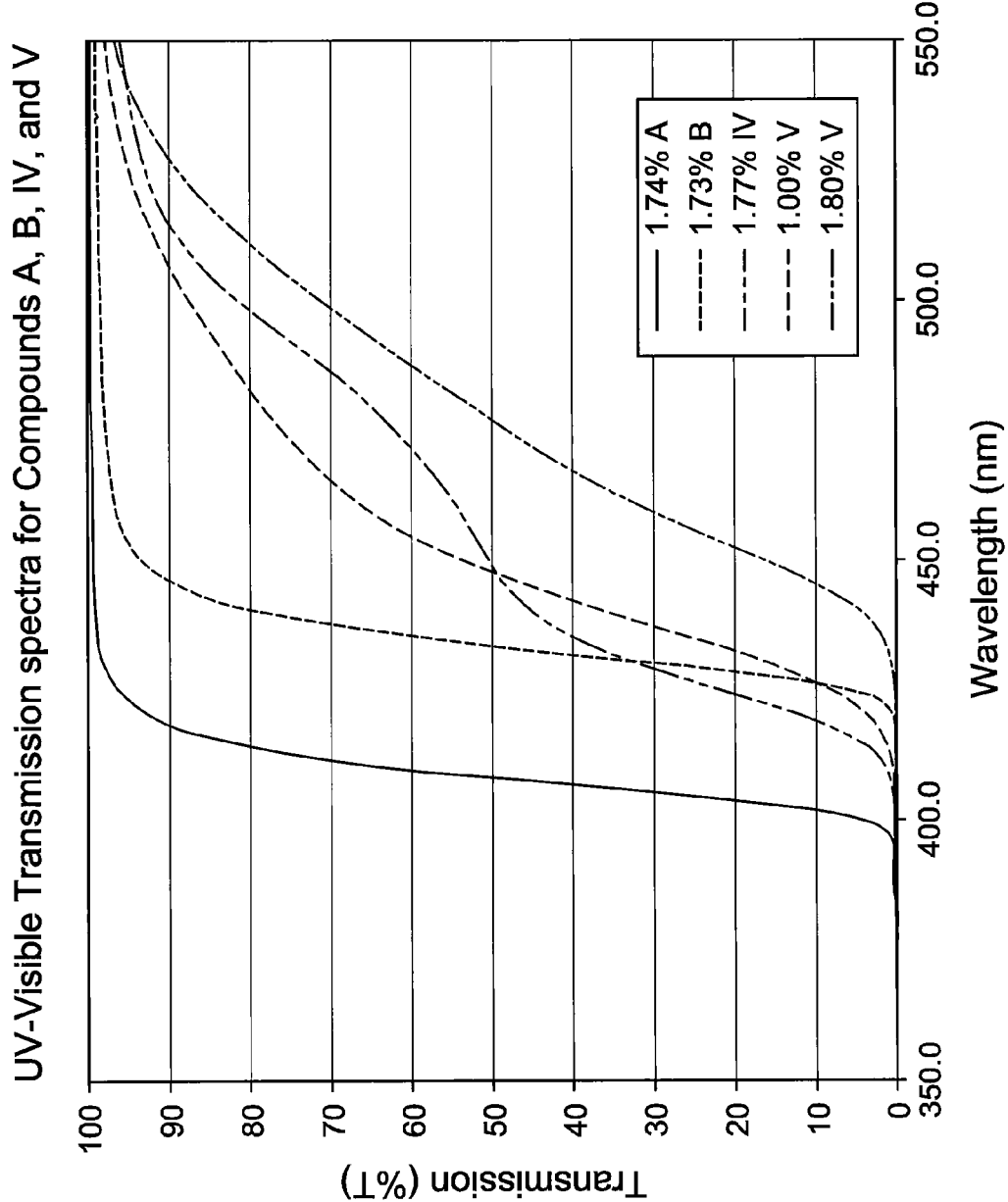

UV-ABSORBERS FOR OPHTHALMIC LENS MATERIALS

CROSS-REFERENCE TO RELATED APPLICATIONS

This application claims priority to U.S. Provisional Patent Application No. 61/080,864, filed Jul. 15, 2008, the entire contents of which are incorporated herein by reference.

FIELD OF THE INVENTION

This invention is directed to ophthalmic lens materials. In particular, this invention relates to ultraviolet light absorbers that are suitable for use in ophthalmic lens materials.

BACKGROUND OF THE INVENTION

Many UV light absorbers are known as ingredients for polymeric materials used to make ophthalmic lenses and, in particular, intraocular lenses. UV absorbers are preferably covalently bound to the polymeric network of the lens material instead of simply physically entrapped in the material to prevent the absorber from migrating, phase separating or leaching out of the lens material. Such stability is particularly important for implantable ophthalmic lenses where the leaching of the UV absorber may present both toxicological issues and lead to the loss of UV blocking activity in the implant.

Numerous copolymerizable benzatriazole, benzophenone and triazine UV absorbers are known. Many of these UV absorbers contain conventional olefinic polymerizable groups, such as methacrylate, acrylate, methacrylamide, acrylamide or styrene groups. Copolymerization with other ingredients in the lens materials, typically with a radical initiator, incorporates the UV absorbers into the resulting polymer chain. Incorporation of additional functional groups on a UV absorber may influence one or more of the UV absorber's UV absorbing properties, solubility or reactivity. If the UV absorber does not have sufficient solubility in the remainder of the ophthalmic lens material ingredients or polymeric lens material, the UV absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

In addition to blocking UV light, some ophthalmic lenses also block blue light. See, for example, U.S. Pat. Nos. 5,470,932 and 5,543,504. These lenses block both types of light by using two chromophores: a UV absorber and a yellow dye.

There is a need for UV absorbers that are suitable for use in implantable ophthalmic lenses and are capable of blocking not only UV light (400 nm and below) but also blocking at least some light between 400-450 nm.

SUMMARY OF THE INVENTION

The present invention provides UV absorbers that block not only UV light but also light in the 400-450 nm range. These UV absorbers are suitable for use in ophthalmic devices, including contact lenses, and are particularly useful in implantable lenses, such as intraocular lenses (IOLs). The UV absorbers of the present invention are copolymerizable with other ingredients in ophthalmic device formulations.

BRIEF DESCRIPTION OF THE DRAWINGS

FIG. 1 shows the UV/VIS spectra of various UV absorbers.

DETAILED DESCRIPTION OF THE INVENTION

Unless indicated otherwise, all ingredient amounts expressed in percentage terms are presented as % w/w.

The UV absorbers of the present invention have the structure shown in formula I.

(I)

wherein:
$X_1$ and $X_2$ independently are nothing, H, Cl, F, Br, I, O, S, $NR_{11}$, $PR_{11}$, $Si(R_{11})_2$, $Sn(R_{11})_2$, $BR_{11}$, or a polymerizable group of formula Ia (below);

$R_1$ and $R_3$ independently are nothing, H, optionally substituted $C_1$-$C_{12}$ alkyl, optionally substituted $C_1$-$C_{12}$ cycloalkyl, optionally substituted phenyl, or optionally substituted naphthyl, wherein the optional substituents independently are $C_1$-$C_6$ alkyl, $C_1$-$C_6$ alkoxy, OH, —Si$(CH_3)_3$, Cl, F, Br, I, —$(CH_2CH_2O)_n$—$R_{12}$, or —$(CH_2CH(CH_3)O)_nR_{12}$;

$R_2$ is nothing, optionally substituted $C_1$-$C_{12}$ alkyl, or (—$CH_2CH_2O$—$)_n$, wherein the optional substituents are $C_1$-$C_6$ alkyl, $C_1$-$C_6$ alkoxy, OH, —Si$(CH_3)_3$, Cl, Br, F, I, —$(CH_2CH_2O)_n$—$R_{11}$, or —$(CH_2CH(CH_3)O)_nR_{11}$; provided that if $R_2 \neq$ nothing, then the resulting ring containing $R_2$ may be saturated or unsaturated;

n=1 to 10;

$R_4$, $R_5$, and $R_6$ independently are a polymerizable group of formula Ia (below), H, optionally substituted $C_1$-$C_{12}$ alkyl, optionally substituted $C_1$-$C_{12}$ cycloalkyl, optionally substituted phenyl, or optionally substituted naphthyl, wherein the optional substituents independently are $C_1$-$C_6$ alkyl, $C_1$-$C_6$ alkoxy, OH, —Si$(CH_3)_3$, Cl, F, Br, I, —$(CH_2CH_2O)_n$—$R_{12}$, or —$(CH_2CH(CH_3)O)_nR_{12}$;

the polymerizable group of formula Ia is:

(Ia)

$X_3$ is nothing, O, S, $NR_{11}$, $PR_{11}$, $BR_{11}$, or $Si(R_{11})_2$;

$R_7$ is $C_1$-$C_6$ alkyl, $C_1$-$C_6$ alkene, $(CH_2CH_2O)_n$, $(CH_2CH(CH_3)O)_n$, or $CH_2CH_2CH_2(Si(CH_3)_2O)_n Si(CH_3)_2CH_2CH_2CH_2$;

$X_4$ is nothing, O, NR11, S, —C(=O)O—, or —C(=O)$NR_{12}$; provided that if $X_4$ is nothing if $R_7$ is $(CH_2CH_2O)_n$ or $(CH_2CH(CH_3)O)_n$;

$R_8$ is nothing, C(=O), C(=O)$C_jH_{2j}$, $C_1$-$C_6$ alkyl, phenyl, $C_1$-$C_6$ alkylphenyl, $C_1$-$C_4$ alkyl-C(=O)O—, $C_1$-$C_4$ alkyl-O—C(=O)—, $C_1$-$C_4$ alkyl-$NR_{12}$—C(=O)—, $C_1$-$C_4$ alkyl-C(=O)—$NR_{12}$—, $C_1$-$C_4$ alkyl-O—C(=O)—$NR_{12}$—, or $C_1$-$C_4$ alkyl-O—C(=O)—$NR_{12}$-;

$R_9$ is H or methyl;
$R_{10}$ is H, $C_1$-$C_6$ alkyl, or phenyl;
j is 1-6;
$R_{11}$ is H, —$Si(CH_3)_3$, optionally substituted $C_1$-$C_{12}$ alkyl; optionally substituted $C_1$-$C_{12}$ cycloalkyl, optionally substituted phenyl, or optionally substituted naphthyl, wherein the optional substituents can be independently $C_1$-$C_6$ alkyl, $C_1$-$C_6$ alkoxy, OH, —$Si(CH_3)_3$, Cl, F, Br, I, or —$(CH_2CH_2O)_n$—$R_{12}$, or —$(CH_2CH(CH_3)O)_nR_{12}$; and
$R_{12}$=H, —$Si(CH_3)_3$, or $C_1$-$C_6$ alkyl.

Preferably,
$X_1$ and $X_2$ independently are nothing, H, Cl, F, Br, I, O, or a polymerizable group of formula Ia;
$R_1$ and $R_3$ independently are nothing, H, or optionally substituted $C_1$-$C_{12}$ alkyl, wherein the optional substituents independently are $C_1$-$C_6$ alkyl, $C_1$-$C_6$ alkoxy, OH, Cl, F, Br, or I;
$R_2$ is nothing, or optionally substituted $C_1$-$C_{12}$ alkyl, wherein the optional substituents are $C_1$-$C_6$ alkyl, $C_1$-$C_6$ alkoxy, OH, Cl, Br, F, or I; provided that if $R_2 \neq$ nothing, then the resulting ring containing $R_2$ may be saturated or unsaturated;
n=1 to 10;
$R_4$, $R_5$, and $R_6$ independently are a polymerizable group of formula Ia, H, or optionally substituted $C_1$-$C_{12}$ alkyl, wherein the optional substituents independently are $C_1$-$C_6$ alkyl, $C_1$-$C_6$ alkoxy, OH, Cl, F, Br, or I;
the polymerizable group of formula Ia is:

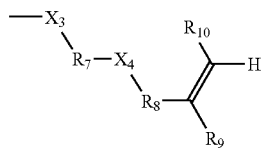

(Ia)

$X_3$ is nothing, O, S, or $NR_{11}$;
$R_7$ is $C_1$-$C_6$ alkyl, or $C_1$-$C_6$ alkene;
$X_4$ is nothing, O, NR11, S, or —C(=O)O—;
$R_8$ is nothing, C(=O), C(=O)$C_jH_{2j}$, $C_1$-$C_6$ alkyl, $C_1$-$C_4$ alkyl-C(=O)O—, or $C_1$-$C_4$ alkyl-O—C(=O)—;
$R_9$ is H or methyl;
$R_{10}$ is H, $C_1$-$C_3$ alkyl;
j is 1-6;
$R_{11}$ is H, —$Si(CH_3)_3$, or optionally substituted $C_1$-$C_6$ alkyl; wherein the optional substituents can be independently $C_1$-$C_6$ alkyl, $C_1$-$C_6$ alkoxy, OH, Cl, F, Br, or I; and
$R_{12}$=H or $C_1$-$C_6$ alkyl.

More preferably,
$R_1$, $R_2$, and $X_3$=nothing;
$X_1$ is Cl;
$R_3$ is nothing;
$X_2$ is a polymerizable group of formula Ia;
$R_7$ is a $C_1$-$C_4$ alkyl group;
$X_4$ is O;
$R_8$ is C=O;
$R_9$ is H or methyl;
$R_{10}$ is H;
$R_4$ and $R_6$ independently are $C_1$-$C_6$ t-alkyl or $C_1$-$C_4$ alkoxy; and
$R_5$ is H.

Most preferably,
$R_1$, $R_2$, and $X_3$=nothing;
$X_1$ is Cl;
$R_3$ is nothing;
$X_2$ is a polymerizable group of formula Ia;
$R_7$ is —$(CH_2)_3$—;
$X_4$ is O;
$R_8$ is C=O;
$R_9$ is methyl;
$R_{10}$ is H;
$R_4$ and $R_6$ are t-butyl; and
$R_5$ is H.

Accordingly, the most preferred compound of generic formula I is represented by structural formula III.

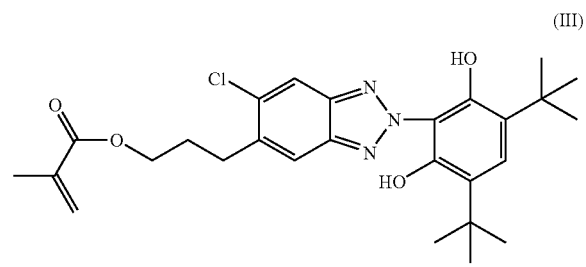

(III)

Two representative non-polymerizable compounds of the present invention are compounds (IV) and (V):

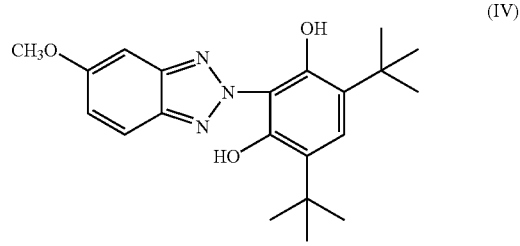

(IV)

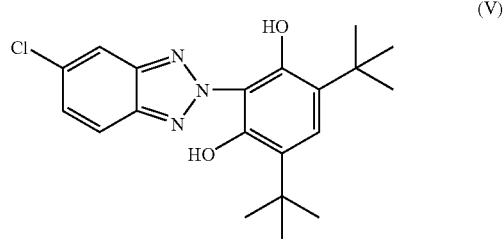

(V)

Compounds of formula (I) can be prepared using methods known in the art. For example, a synthetic pathway to prepare the dihydroxy benzotriazoles of the present invention is shown in Scheme 1. This process starts with the diazotization reaction of the appropriately substituted 2-nitroaniline compound (VI) to form the diazonium salt (VII). The diazonium salt intermediate is immediately reacted with the target hydroxyphenol or resorcinolic compound (VIII) via azo coupling reaction to make the nitro azo intermediate compound (IX), which can be isolated and purified or often used in crude form. The azo coupling step is followed by the reduction of the nitro azo intermediate (IX) with alkaline glucose solution and zinc powder, which closes the triazole ring providing the desired dihydroxy benzotriazole compound (X).

Scheme 1. Generic 2,6-dihydroxyphenyl-2H-benzotriazole synthesis

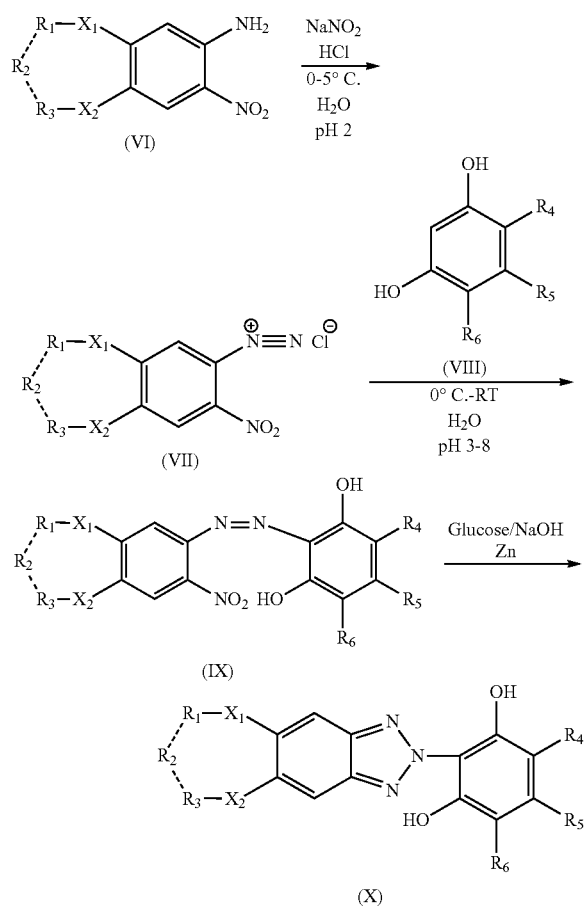

In general, reaction Scheme 1 works best when $R_1$, $R_3$, $R_4$, $R_5$, or $R_6$ does not already contain an ester, carbonate, carbamate, or isocyanate group. In those cases, the polymerizable group (containing an ester, carbonate, carbamate, or isocyanate group) should be added after the Scheme 1 reaction sequence. For example, if $R_3$ included an ester group, such as the case when $R_3$ is the polymerizable group of formula Ia and contains an acrylate or methacrylate group, the substituted 2-nitroaniline reactant (VI) may have an omega-hydroxyl alkylene group (e.g., $-CH_2-CH_2CH_2OH$) in place of the desired $R_3$ group during the reaction sequence of Scheme 1. The desired polymerizable $R_3$ group could then be added via a dehydrohalogenation reaction using acryloyl- or methacryloyl chloride, for example.

In general, the specialty substituted 2-nitroanilines, denoted as (VI) in Scheme 1 above, as well as, the specialty target resorcinolic compound (VIII), may be synthesized by methods and techniques known to those skilled in the art. For example, the synthesis of a substituted 2-nitroaniline is shown in Scheme 2. The 4-(3-hydroxypropyl)-5-chloro-2-nitroaniline (XIV) can be prepared by the iodination of 5-chloro-2-nitroaniline (XI, Aldrich Chemical Co.) by reaction with N-iodosuccimide (NIS) to provide the iodo-substituted chloro-ortho-nitroaniline (XII). Then intermediate XII is reacted with allyl alcohol in the presence of a suitable palladium catalyst to make intermediate XIII, which is then reduced with sodium borohydride ($NaBH_4$) to complete the substitution of the iodine by the 3-hydroxypropyl moiety to give the desired ortho-nitroaniline starting material (XIV). After preparation, Compound XIV may be used as the starting material, in place of the generic VI compound, needed for the benzotriazole synthesis (Scheme 1).

Scheme 2. Specific synthetic pathyway to prepare 4-(3-hydroxypropyl)-5-chloro-2-nitroaniline starting material (XIV)

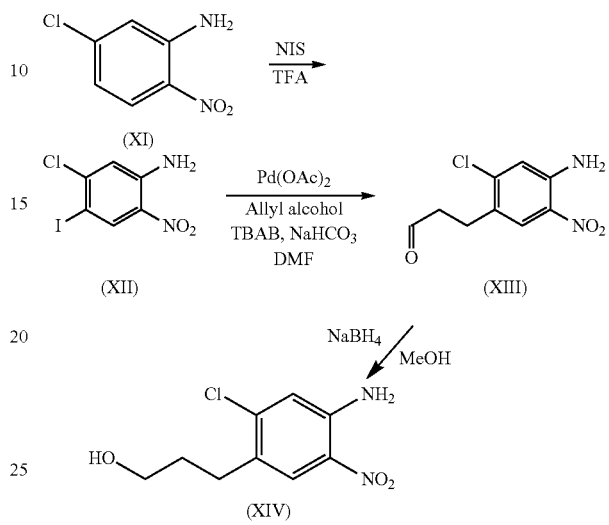

The UV absorbers of the present invention are particularly suitable for use in IOLs. IOL materials will generally contain from 0.1 to 5% (w/w) of a UV absorber of formula I. Preferably, IOL materials will contain from 0.1 to 2% (w/w) of a UV absorber of the present invention.

Ophthalmic device materials are prepared by copolymerizing the UV absorbers of the present invention with other ingredients, such as device-forming materials, cross-linking agents, and blue-light blocking chromophores.

Many device-forming monomers are known in the art and include both acrylic and silicone-containing monomers among others. See, for example, U.S. Pat. Nos. 7,101,949; 7,067,602; 7,037,954; 6,872,793 6,852,793; 6,846,897; 6,806,337; 6,528,602; and 5,693,095. In the case of IOLs, any known IOL device material is suitable for use in the compositions of the present invention. Preferably, the ophthalmic device materials comprise an acrylic or methacrylic device-forming monomer. More preferably, the device-forming monomers comprise a monomer of formula II:

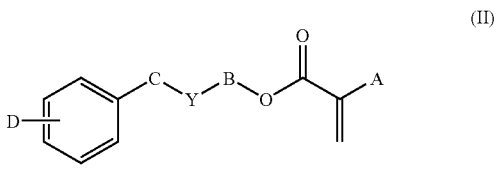

where in formula II:
A is H, $CH_3$, $CH_2CH_3$, or $CH_2OH$;
B is $(CH_2)_m$ or $[O(CH_2)_2]_z$;
C is $(CH_2)_w$;
m is 2-6;
z is 1-10;
Y is nothing, O, S, or NR', provided that if Y is O, S, or NR', then B is $(CH_2)_m$;
R' is H, $CH_3$, $C_{n'}H_{2n'+1}$ (n'=1-10), iso $-OC_3H_7$, $C_6H_5$, or $CH_2C_6H_5$;
w is 0-6, provided that m+w≦8; and
D is H, $C_1$-$C_4$ alkyl, $C_1$-$C_4$ alkoxy, $C_6H_5$, $CH_2C_6H_5$ or halogen.

Preferred monomers of formula II are those wherein A is H or $CH_3$, B is $(CH_2)_m$, m is 2-5, Y is nothing or O, w is 0-1, and D is H. Most preferred are 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

Monomers of formula II are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

Device materials generally comprise a total of at least about 75%, preferably at least about 80%, of device-forming monomers.

In addition to a UV absorber of formula I and a device-forming monomer, the device materials of the present invention generally comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C(=O)O$—$(CH_2CH_2O)_p$—$C(=O)C(CH_3)$=$CH_2$ where p=1-50; and $CH_2$=$C(CH_3)C(=O)O(CH_2)_tO$—$C(=O)C(CH_3)$=$CH_2$ where t=3-20; and their corresponding acrylates. A preferred cross-linking monomer is $CH_2$=$C(CH_3)C(=O)O$—$(CH_2CH_2O)_p$—$C(=O)C(CH_3)$=$CH_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 0.1-17% (w/w).

Suitable polymerization initiators for device materials containing a UV absorber of the present invention include thermal initiators and photoinitiators. Preferred thermal initiators include peroxy free-radical initiators, such as t-butyl (peroxy-2-ethyl)hexanoate and di-(tert-butylcyclohexyl)peroxydicarbonate (commercially available as Perkadox® 16 from Akzo Chemicals Inc., Chicago, Ill.). Initiators are typically present in an amount of about 5% (w/w) or less. Because free-radical initiators do not become chemically a part of the polymers formed, the total amount of initiator is customarily not included when determining the amounts of other ingredients.

The device materials containing a UV absorber of the present invention may also contain a reactive colorant. Suitable reactive blue-light absorbing compounds include those described in U.S. Pat. No. 5,470,932. Blue-light absorbers are typically present in an amount from about 0.01-0.5% (weight).

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use in other ophthalmic devices, such as contact lenses, keratoprostheses, and corneal inlays or rings.

The invention will be further illustrated by the following examples, which are intended to be illustrative, but not limiting.

EXAMPLE 1

Synthesis of N-2-[2',6'-Diydroxy-3',5'-di-tert-butylphenyl]-5-methoxy-2H-benzotriazole ("Compound IV")

a. Preparation of nitro azo Intermediate: 2-(4'-methoxy-2'-nitrophenylazo)-4,6-di-tert-butylresorcinol In general, the reaction Scheme 1 shown above, may be applied to this specific synthetic sequence. About 3.025 grams (17.99 mmoles) of 4-methoxy-2-nitroaniline (Aldrich Chemical Co., see Scheme 1, structure VI, where R1 and R2 each=nothing, X1=H, X2=O, and R3=$CH_3$) was dissolved in a mixed solvent of 40 mL tetrahydrofuran (THF), 20 mL water, which was acidified with 3.3 mL of 48% aqueous tetrafluoroboronic acid ($HBF_4$). The reaction vessel used was a 500 mL jacketed reaction flask connected to a circulating cooling bath keeping the reaction temperature from about −1 to 4° C. A solution of 1.241 grams (17.99 mmoles) of sodium nitrite was prepared in 20 mL of water. The sodium nitrite solution was cooled in an ice bath and added dropwise to the reaction mixture. The reaction temperature was kept between −0.3 to 0.3° C. during the $NaNO_2$ addition and the reaction pH was maintained between 2-3 by the addition of cold aqueous 48% $HBF_4$ dropwise into the reaction mixture. After the addition of sodium nitrite was complete the reaction mixture was stirred for about 10 minutes.

A solution of 4.197 grams (18.88 mmoles=1 equivalent+5% excess) of 4,6-di-tert-butylresorcinol (Fluka Chemical Co., Scheme 1, Compound VIII, where R4=R6=tert-butyl, R5=H) was dissolved in a mixed solvent consisting of 20 mL of water and 20 mL of tetrahydrofuran (THF) in a 100 mL glass beaker with the aid of a magnetic stirrer and stirbar. A 1.51 mL aliquot of 50% w/w aqueous NaOH was added to the beaker. After dissolving, the beaker was cooled in an ice bath and transferred cold into a 500 mL separatory funnel and the 4,6-di-tert-butylresorcinol solution of was added to the reaction mixture dropwise over a 45 minutes interval. During the addition, the formation of a red precipitant was observed in the reaction mixture and the reaction temperature was maintained around 0° C. After the addition was complete the pH was found to be about 3. The pH of the reaction mixture was raised to about 9 by the dropwise addition of 50% aqueous sodium hydroxide solution and then back down to pH 6 by addition of $HBF_4$. The reaction was kept at 0-2° C. overnight (16 hours) and then allowed to slowly warm up to room temperature with continue stirring over a two hour interval.

After the reaction mixture reached ambient temperature, the red solid precipitant was filtered from the reaction mixture with a 250 mL fritted filter and the filtrate washed 3 times with 100 mL portions of cold water. The red solid (nitro azo product) was air dried on the filter for about 30 minutes and was found to be about 6.673 grams of crude product (Yield 92.4%). The HPLC analysis of the crude product using a C18 column and acetonitrile:water gradient mobile phase, indicated the purity of the crude nitro azo product (see Scheme 1, Compound IX, where R1=R2=nothing, X1=H, X2=O, R3=$CH_3$, R4=R6=tert-butyl, and R5=H) to be 70.15%.

b. Preparation of benzotriazole, Compound IV

The crude nitro azo product from above, 2-(4'-methoxy-2'-nitrophenylazo)-4,6-di-tert-butylresorcinol, was used without further purification in the next reaction step. About 2.007 grams (5 mmoles) of crude nitro azo product was dissolved in 50 mL of reagent alcohol in a 250 mL 3-necked round bottom flask, which was equipped with two rubber septa, a 125 mL addition funnel, and a magnetic stirbar. Gentle heating to 50° C. with a water bath was required to fully dissolve the nitro azo compound into the ethanol, then heating was stopped. Using a 6" needle the solution and reaction vessel were purged with nitrogen. A solution containing 1.803 grams (10.01 mmoles) of glucose (Aldrich Chemical Co.) in 50 mL aqueous 2 N NaOH was added to the addition funnel and purged with nitrogen. The glucose solution was added dropwise to the reaction flask with stirring over a 30 minute interval. After the addition of the glucose solution, the reaction mixture was stirred overnight (22 hours) at room temperature.

The next day 3.292 grams (50.36 mmoles) of acid washed zinc powder (100 mesh, 99.95%, Aldrich Chemical Co.) was added to the reaction mixture with about 10 mL of water. After the zinc addition the reaction mixture was purged with nitrogen and stirred for 38.5 hours at room temperature. Then the reaction flask was heated to 50° C. in a water bath for 2 hours, Heating was discontinued and the reaction mixture slowly cooled to room temperature. The excess zinc from the reaction mixture was filtered off using a 100 mL fritted filter and the zinc washed with 50 mL of warm reagent alcohol (ethanol). The reaction supernatant was transferred into a 250 mL beaker and was neutralized from pH 14 to 7 by the addition of 100 mL of 2 N HCl, followed by dropwise addition of 2 N HCl to further adjust the pH to 4.

The neutralized filtrate solution was poured into a 500 mL separatory funnel and 100 mL of aqueous 30% NaCl solution was added. The solution was extracted 4 times with 50 mL portions of toluene. The toluene extracts were combined and washed 4 times with 100 mL portions of water and the combined toluene extracts were dried for 2 hours over $MgSO_4$. The combined toluene extracts were filtered into a 1000 mL round-bottomed flask and the solvents were removed under vacuum (rotary evaporator), leaving a brown residue in the flask. HPLC analysis of the residue indicated a new peak at 22.9 minutes with a UV spectral max at 343 nm. The residue was left in the round bottomed flask and 20 mL of methylene chloride was added to dissolve the residue.

About 6 grams of alumina was added to the flask and the methylene chloride was removed under vacuum (rotary evaporator), leaving the alumina coated with the residue. The flask was cleaned with an additional 5 grams of alumina, which was combined and mixed with the first portion of residue-coated alumina. The reaction residue coated on alumina (11 grams) was placed onto an alumina column (6 grams of sand and 60 grams of alumina) for column chromatography purification in a 25×350 mm fritted glass column. The column was successively eluted with 4.8 L of hexane, followed by 800 mL of 50:50 hexane:methylene chloride. From this 5 fractions were collected and HPLC analysis gave the composition of the 22.9 minute peak, correlated to the desired product, to be from 68% to 28% (in last fraction), but considerable residue remained on the column.

Therefore, a second column chromatography run was performed as described above, but using a column composed of 5 grams of sand+200 grams of silica gel+the alumina coated with residue from the combined fractions of the first run. The column was successively eluted with 1900 mL of hexane, 1900 mL of 90:10 hexane:methylene chloride, 1000 mL of 70:30 hexane:methylene chloride, and 2000 mL o 50:50 hexane:methylene chloride. The first fraction was clear with no residue, but the second fraction was a pale yellow solution, which gave a pale yellow, light green solid residue upon removal of the solvents under vacuum. HPLC analysis of the second fraction, indicated it to have a composition of 98.7% of the 22.9 minute peak with UV spectral maxima at 289 and 345 nm, believed to be the desired product, Compound IV. Subsequent fractions had compositions by HPLC analysis with small amounts of the desired product and were discarded. The second fraction provided 61.5 mg of Compound IV (Yield 1.25%).

Further spectroscopic analysis by NMR and LC-MS provided data consistent with the chemical structure of Compound IV. The $^1$H-NMR spectrum provided a singlet at 1.40 ppm, integral 18.1H for the 6 equivalent t-butyl methyl groups, a singlet at 3.86 ppm, integral 3.02H for the methoxy group, a singlet at 11.70 ppm, integral 1.98H for the 2 equivalent resorcinol hydroxyl groups, four aromatic signals at 7.0-7.8 ppm with a total integral value of 4.04 H for the 3 protons on the benzotriazole ring and the one on the resorcinolic ring.

Likewise, the $^{13}$C NMR had three aliphatic signals: at 29.77 ppm for the 6 equivalent tert-butyl methyl groups (upright signal in DEPT), at 35.10 ppm for the 2 equivalent tertiary central carbons (disappears in DEPT) of the 2 equivalent tert-butyl moieties, and a singlet at 55.76 ppm for the methoxy carbon (upright signal in DEPT). Furthermore, the 13C NMR spectrum had 10 aromatic signals at 93.72, 114.84, 117.61, 123.19, 125.44, 127.16, 136.22, 141.43, 147.23 (2 equivalent C—OH), and 160.13 ppm (C—OMe). However, all of the quaternary aromatic signals disappeared in the DEPT spectra except for 93.72, 117.62, 123.20, and 125.44 ppm (all upright in DEPT), which is consistent with 4 aromatic C—H carbon atoms in the structure.

The LC-MS analysis showed a major peak in the chromatogram at 6.13 minutes with a mass spectrum base peak at 370 amu. Since the molecular weight of Compound IV is 369 and, then the base peak at 370 amu correlates to the molecular ion+a proton ($M^+$+H). Therefore, the mass spectral base peak at 370 amu gave a direct confirmation of the structure of Compound IV.

EXAMPLE 2

Synthesis of N-2-[2',6'-Diydroxy-3',5'-di-tert-butylphenyl]-5-chloro-2H-benzotriazole ("Compound V")

a. Preparation of nitro azo Intermediate: 2-(4'-chloro-2'-nitrophenylazo)-4,6-di-tert-butylresorcinol In general, the reaction Scheme 1 shown above, may be applied to this specific synthetic sequence. About 5.279 grams (30.59 mmoles) of 4-chloro-2-nitroaniline (Aldrich Chemical Co., see Scheme 1, structure VI, where R1, R2, and R3 each=nothing, X1=H, X2=Cl) was dissolved in 200 mL tetrahydrofuran (THF) in a 500 mL jacketed reaction flask connected to a circulating cooling bath keeping the reaction temperature from −1 to 4° C. The pH was adjusted to 1.3-2.5 by the addition of cold 12 N HCl dropwise into The reaction solution. A solution of 2.113 grams (30.62 mmoles) of sodium nitrite was prepared in 20 mL of water. The sodium nitrite solution was cooled in an ice bath and added dropwise to the reaction mixture with continuous monitoring of the reaction pH and temperature with addition of cold HCl as needed to maintain the pH to about 1.3-2.5. After the addition of sodium nitrite was complete the reaction mixture was stirred for about 10 minutes.

A solution of 6.804 grams (30.60 mmoles) of 4,6-di-tert-butylresorcinol (Fluka Chemical Co., Scheme 1, Compound VIII, where R4=R6=tert-butyl, R5=H) was dissolved into 40 mL of tetrahydrofuran (THF) in a 100 mL glass beaker with the aid of a magnetic stirrer and stirbar. After dissolving, the beaker was cooled in an ice bath and transferred cold into a 500 mL separatory funnel. About 4 drops of 2.5 N sodium hydroxide were added to the funnel. The solution of II was added to the reaction mixture dropwise from the separatory funnel over a 30 minutes interval. During the addition the reaction temperature was maintained between 0-2° C. After the addition was complete the pH was found to be about 3. The pH of the reaction mixture was raised to about 8 by the addition of 2.5 N sodium hydroxide dropwise to the reaction. The reaction was allowed to continue stirring for at least two hours and was allowed to slowly warm up to room temperature.

After the reaction mixture reached ambient temperature, the mixture was poured into a 1000 ml round bottom flask. The flask was placed on the rotary evaporator and the THF was removed under vacuum. A red solid precipitated from the reaction mixture end was filtered off using a 250 ml fritted funnel. The solid was washed with 200 ml of cold water. The crude red solid (nitro azo product) was weighed to obtain an approximate yield of the reaction: 11.457 grams, 92.2%. The HPLC analysis of the crude product using a C18 column and acetonitrile:water gradient mobile phase indicated the purity of the crude nitro azo product (see Scheme 1, Compound IX, where R1=R2=R3=nothing, X1=H, X2=Cl, R4=R6=tert-butyl, and R5=H) to be 87.84%.

Column chromatography was performed to purify the crude azo compound. Separate, 2.5 and 5.0 grams of nitro azo product were dissolved into 20 mL of methylene chloride and evaporated onto 10 grams of silica gel. A column was prepared by placing 10 grams of sand, 60 grams of silica gel, 30 grams of alumina, and 10 grams of sand into a 300 X. 25 mm fritted glass column. The silica gel coated with the azo product was placed at the top of the column and the column in each run was eluted successively with: hexane, methylene chloride, methylene chloride:acetonitrile, acetonitrile, and ethanol. Fractions were collected and concentrated under vacuum (rotary evaporator) and analyzed by HPLC. The first fraction from each column run contained the highest amount of purified nitro azo compound and were combined. The nitro azo compound from the combined fractions was recrystallized from 80:20 ethanol:water to give 1.933 grams (13.6% yield) and HPLC analysis indicated a purity of 87.4%.

b. Preparation of benzotriazole Compound V

For the next synthetic step, 0.904 grams (2.23 mmoles) of purified nitro azo compound was dissolved in 25 mL of reagent alcohol and the solution placed into a 250 mL 3-necked round bottom flask equipped with two rubber septa, a 125 mL addition funnel, and a magnetic stirbar. Using a 6" needle the solution and reaction vessel were purged with nitrogen. A solution containing 0.804 grams (4.46 mmoles) of glucose (Aldrich Chemical Co.) in aqueous 2 N NaOH was added to the addition funnel and purged with nitrogen. The glucose solution was added to the reaction flask containing the nitro azo compound with stirring over a 25 minute interval. After the addition of the glucose solution, stirring of the reaction mixture was continued overnight (16 hours) at room temperature.

The next day 1.470 grams (22.83 mmoles) of acid washed zinc power (100 mesh, 99.95%, Aldrich Chemical Co.) was added to the reaction mixture with about 20 mL of water. After the zinc addition the reaction mixture was stirred for 4 hours at room temperature. The color of the reaction mixture changed from dark brown to dark red. Then the reaction flask was heated to 50° C. in a water bath for 2.5 hours, which caused the color to turn from dark red to a golden tan color. Heating was discontinued and the reaction mixture was further stirred overnight (16 hours) at room temperature.

The reaction mixture was passed through a fritted filter to remove the excess zinc powder. To the filtrate solution was added 50 mL of aqueous 1 N HCl solution to adjust the solution to a neutral pH and 100 mL of saturated aqueous NaCl solution was added. The pH was taken and an additional 12 N HCl reagent was added to adjust the pH further down to pH 4. The neutralized and salinated filtrate solution was added to a 500 mL sepratory funnel and was extracted 3 times with 50 mL portions of toluene. The toluene extracts were combined and washed 3 times with 100 mL portions of water and the combined toluene extracts were dried over $MgSO_4$. The combined toluene extracts were filtered into a 500 mL flask and the toluene was removed under vacuum (rotary evaporator), leaving a brown residue in the flask. The residue was dissolved in 20 mL of methylene chloride and 10 grams of silica gel was added to the flask and the methylene chloride was removed under vacuum. The silica gel, coated with the crude reaction residue, was placed onto an alumina column (5 grams of sand, 30 grams of alumina+5 grams of sand) for column chromatography purification. The column was successively eluted with hexane. The initial fractions from the column were a canary yellow color and were analyzed individually by HPLC. The analysis revealed a major peak at 25 minutes retention time with a UV spectral $\lambda_{max}$ at 340 nm. Since the first 4 fractions were relatively high in concentration of the 25 min peak (85 to 98%, 350 nm chromatogram), these fractions were combined into a single flask. The solvent was removed under vacuum (rotary evaporator) leaving 0.102 grams of a bright yellow solid, yield 12.2%.

Further spectroscopic analysis by NMR and LC-MS provided data consistent with the chemical structure of Compound V. The $^1$H-NMR spectrum provided a singlet at 1.40 ppm, integral 18.5H for the 6 equivalent t-butyl methyl groups, a singlet at 11.57 ppm, integral 1.95H for the 2 equivalent resorcinol hydroxyl groups, aromatic singlet at 7.42 ppm, integral 1.00H for the lone proton on the resorcinol moiety, and 3 aromatic signals: a doublet of doublet at 7.88 ppm, integral 1.02H, $J_{4H7H}$=2.0 Hz, $J_{4H6H}$=0.8 Hz for the 4-proton, a second aromatic doublet of doublets at 7.82 ppm, integral 1.02H, $J_{6H7H}$=9.0 Hz, $J_{6H4H}$=0.8 Hz for the 6-proton, and a third aromatic doublet of doublets at 7.43 ppm, integral 1.12H, $J_{7H6H}$=9.0 Hz, $J_{7H4H}$=0.8 Hz for the 7-proton, respectively, on the benzotriazole moiety. Likewise, the $^{13}$C NMR had two aliphatic signals at 29.74 ppm for the 6 equivalent tert-butyl methyl (upright signal in DEPT) groups and at 35.15 ppm for the 2 equivalent tertiary central carbons (disappears in DEPT) of the tert-butyl moieties and 10 aromatic signals at 114.5, 115.92, 117.98, 126.51, 127.,45, 129.79, 134.24, 138.75, 140.62 (C—Cl), 147.55 (2 equivalent C—OH), but all the quaternary aromatic signals disappeared in the DEPT spectra except for 115.91, 117.98, 126.62, and 129.78 ppm, which is consistent with 4 C—H carbons in the structure. The LC-MS analysis showed two peaks in the chromatogram at 3.96 and 7.59 min with the 7.59 min peak giving a mass spectrum with a base peak at 316 amu and peaks from 317-319 amu, which correlate to the molecular ion (373 & 375 amu) with a chlorine substituent (75% $^{35}$Cl & 25% $^{37}$Cl). Therefore, the loss of an isobutylene group (56 amu) or t-butyl radical (57 amu) gives rise to a base peak at 316 amu (373-57), 317 (373-56), 318 (375-57), and 319 (375-56). These are all spectral data consistent with the structure of Compound V.

EXAMPLE 3

Synthesis of N-2-[2',6'-Diydroxy-3',5'-di-tert-butylphenyl]-5-chloro-6-(3"-methacryloyloxypropyl)-2H-benzotriazole ("Compound III")

a. Preparation of Intermediate 4,6-di-tert-butyl-[4'-chloro-5'-(3"-hydroxypropyl)-2'-nitrophenylazo] resorcinol The general Scheme 1 for may be applied for the overall synthesis of this specific nitro azo intermediate following the procedure provided in Example 2. About 30 mmoles) of 4-chloro-5-(3'-hydroxypropyl)-2-nitroaniline, see Scheme 1, structure VI (where R2, R3 and X1 each=nothing, R1=3-hydroxypropyl, X2=Cl) can be dissolved in 200 mL tetrahydrofuran (THF) in a 500 mL jacketed reaction flask connected to a circulating cooling bath keeping the reaction temperature from −1 to 4° C. The pH is adjusted to 1.3-2.5 by the addition of cold 12 N HCl dropwise into the reaction solution. A solution of 30 mmoles of sodium nitrite is prepared in 20 mL of water. The sodium nitrite solution is cooled in an ice bath and added dropwise to the reaction mixture with continuous monitoring of the reaction pH and temperature with addition of cold HCl as needed to maintain the pH to about 1.3-2.5. After the addition of sodium nitrite is complete, the reaction mixture should be stirred for about 10 minutes.

A solution of 30 mmoles of 4,6-di-tert-butylresorcinol (Fluka Chemical Co., see Scheme 1, Compound VIII, where R4=R6=tert-butyl, R5=H) may be dissolved in 40 mL of tetrahydrofuran (THF) in a 100 mL glass beaker with the aid of a magnetic stirrer and stirbar. After dissolving, the beaker is cooled in an ice bath and transferred cold into a 500 mL sepatory funnel. About 4 drops of 2.5 N sodium hydroxide should be added to the funnel. The solution of VIII is added to the reaction mixture dropwise from the sepatory funnel over a 30 minute interval. During the addition the reaction temperature is maintained between 0-2° C. After the addition is complete the pH should be about 3. The pH of the reaction mixture is raised to about 8 by the addition of 2.5 N sodium hydroxide dropwise to the reaction. The reaction is allowed to continue stirring for at least two hours and allowed to slowly warm up to room temperature.

After the reaction mixture reaches ambient temperature, the mixture should be poured into a 1000 ml round bottom flask. The flask is placed on the rotary evaporator and the THF was removed under vacuum. A red solid should precipitate from the reaction mixture end can be filtered off using a 250 ml fritted funnel. The solid should be washed with 200 ml of cold water. The crude red solid (nitro azo product) should provide an approximate yield of about 80% of the crude nitro azo compound (see Scheme 1, Compound IX, where R2=R3=X1=nothing, R1=3-hydroxypropyl, X2=Cl, R4=R6=tert-butyl, and R5=H).

Column chromatography may be performed to further purify the crude azo compound. Typically, a column of silica gel-alumina as described above in Example 2 can be effective by coating the nitro azo intermediate on to silica gel, placing on the column and eluting successively with: hexane, methylene chloride, methylene chloride:acetonitrile, acetonitrile, and ethanol.

b. Preparation of Intermediate N-2-[2',6'-Hydroxy-3', 5'-di-tert-butyl-phenyl]-5-chloro-6-(3"-hydroxypropyl)-2H-benzotriazole For the next synthetic step, about 2.2 mmoles of purified nitro azo compound is dissolved in 25 mL of reagent alcohol and the solution placed into a 250 mL 3-necked round bottom flask equipped with two rubber septa, a 125 mL addition funnel, and a magnetic stirbar. Using a 6" needle the solution and reaction vessel are purged with nitrogen. Then a solution containing 4.4 mmoles of glucose (Aldrich Chemical Co.) in aqueous 2 N NaOH should be added to the addition funnel and purged with nitrogen. The glucose solution is added to the reaction flask containing the nitro azo intermediate with stirring over a 25 minute interval. After the addition of the glucose solution, the reaction mixture should be stirred from 6 hours up to 16 hours (overnight) at room temperature.

Afterwards, about 22 mmoles of acid washed zinc power (100 mesh, 99.95%, Aldrich Chemical Co.) should be added to the reaction mixture with about 20 mL of water. After the zinc addition the reaction mixture is stirred for about 4 hours at room temperature. The color of the reaction mixture should change from dark brown to dark red. Then the reaction flask should be heated to 50° C. in a water bath for about 2.5 hours, which may cause the color to turn from dark red to a golden tan color.

Afterwards, the reaction mixture should be passed through a fritted filter to remove the excess zinc powder. Then to the filtrate solution is added 50 mL of aqueous 1 N HCl solution to adjust the solution to a neutral pH and 100 mL of saturated aqueous NaCl solution is also added. The pH should be around 4-6, but if not 12 N HCl reagent can be added to adjust the pH further down to pH 4. Now the neutralized and salinated filtrate solution is added to a 500 mL sepatory funnel and extracted 3 times with 50 mL portions of toluene. The toluene extracts should be combined and washed 3 times with 100 mL portions of water and the combined toluene extracts are dried over MgSO$_4$. The combined toluene extracts were filtered into a 500 mL flask and the toluene is removed under vacuum (rotary evaporator), leaving a brown residue in the flask. The residue should be dissolved in about 20 mL of methylene chloride and 10 grams of silica gel is added to the flask and the methylene chloride is removed under vacuum. The silica gel, coated with the crude reaction residue, is placed onto an alumina column (5 grams of sand, 30 grams of alumina+5 grams of sand) for column chromatography purification. The column is successively eluted with hexane. The initial fractions from the column should be a canary yellow color and should contain the benzotriazole intermediate. After HPLC analysis, fractions containing the benzotriazole intermediate should be combined and the solvent removed under vacuum (rotary evaporator) leaving a bright yellow solid at a typical yield of about 10%. The chemical structure should be confirmed by NMR and mass spectroscopic analysis.

c. Preparation of monomer N-2-[2',6'-Hydroxy-3',5'-di-tert -butyl -phenyl]-5-chloro-6-(3"-methacryloyloxypropyl)-2H-benzotriazole In a 100 mL 3-neck round bottomed flask equipped with a magnetic stirbar, a thermometer and an addition funnel, with a pressure-equalizing side arm, are placed 0.22 mmoles) of the benzotriazole intermediate (see Scheme 1, Compound X, where R2=R3=X1=nothing, R1=3-hydroxypropyl, X2=Cl, R4=R6=tert-butyl, and R5=H), 20 mL of dry toluene, and 0.3 mmole of dry pyridine. A solution of 0.3 mmoles of methacryloyl chloride in 2 mL of toluene is added to the mixture over a 10 minute time interval. The reaction mixture was stirred overnight at ambient temperature (<25° C.). A white precipitate (pyridinium chloride) should be separated by filtration and washed with toluene. The filtrate and washings were combined, washed with 1N hydrochloric acid, water, aqueous sodium bicarbonate and water successively (10 mL portions of each). Then the organic (toluene) layer should be separated from the last washing, transferred into a 50 mL flask, and then dried for 3 hours over anhydrous sodium sulfate. The sodium sulfate is filtered off and the organic layer is concentrated under vacuum by evaporation of toluene on a rotary evaporator. The residue is dissolved in a mixture of 3 mL of methanol and 2 mL of methylene chloride by heating in a water bath at 45° C. The resulting solution is filtered to remove a small amount of insoluble material. The solution is cooled slowly to room temperature, then in a refrigerator and finally by placing in a freezer where the temperature was lowered to about −20° C. The resulting crystals are separated by filtration, washed with 3 mL of cold methanol/methylene chloride (90/10 v/v) and should be dried under vacuum to give >95% pure product, which should be confirmed by HPLC analysis with a yield >80% of Compound III.

EXAMPLE 4

UV-Visible Transmission of Solutions of dihydroxy benzotriazole Compounds

Solutions containing from 1.70 to as much as 1.80% by weight of the benzotriazole compounds listed in Table 1 below were prepared in either chloroform ($CHCl_3$) or dichloromethane ($CH_2Cl_2$). The solutions were prepared by dissolving about 0.018 grams of UV absorber into about 0.982 grams of solvent by weighing to an accuracy of ±0.01 mg. The UV-visible transmission spectrum of each solution was measured. The measurement was performed from 850 to 250 nm in 1-mm quartz cuvettes using a Perkin-Elmer Lambda 35 UV-Visible Spectrophotometer. The results are shown in FIG. 1. From each spectrum, the wavelengths for the 1% T and 10% T cutoff were determined and those values are listed in Table 2.

TABLE 1

| Compound | Structure |
|---|---|
| IV | [structure: 5-methoxy benzotriazole with 2,4-di-tert-butyl-3,6-dihydroxyphenyl] |
| V | [structure: 5-chloro benzotriazole with 3,5-di-tert-butyl-2,6-dihydroxyphenyl] |
| A | [structure: 5-methoxy benzotriazole with tert-butyl, hydroxyphenyl, and propyl methacrylate group] |
| B | [structure: benzotriazole with hydroxyphenyl, methallyl and methyl substituents] |

TABLE 2

UV-Visible transmission data for solutions of benzotriazole compounds

| UV Absorber Compound | Molecular Wt. (MW), mg/mmole | Conc. (wt %) | Estimated Molar conc nmole/mL, M | Transmission cutoff Wavelength in nm | |
|---|---|---|---|---|---|
| | | | | 1% T | 10% T |
| B | 279.3 | 1.74 | 0.0925 | 397.5 | 401.5 |
| A | 439.5 | 1.73 | 0.0584 | 421.5 | 426.0 |
| IV | 369.5 | 1.77 | 0.0711 | 409.5 | 419.0 |
| V | 373.9 | 1.00 | 0.0355 | 414.0 | 426.5 |
| V | 373.9 | 1.80 | 0.0714 | 433.0 | 445.5 |

The dihydroxy benzotriazole compounds, IV and V, illustrate the utility of the dihydroxy benzotriazoles of the present invention for the modulation of UV and violet light in ophthalmic devices, including IOLs.

I claim:
1. A UV absorber of the formula

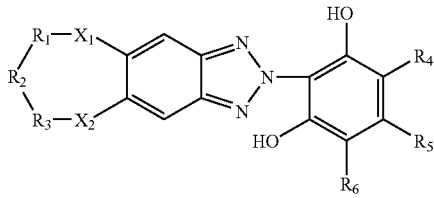

(I)

$R_1$, $R_2$ and $R_3$=nothing;
$X_1$ is Cl;
$X_2$ is a polymerizable group of formula Ia;
the polymerizable group of formula Ia is:

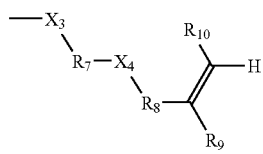

(Ia)

$X_3$ is nothing;
$R_7$ is a $C_1$-$C_4$ alkyl group;
$X_4$ is O;
$R_8$ is C=O;
$R_9$ is H or methyl;
$R_{10}$ is H;
$R_4$ and $R_6$ independently are $C_1$-$C_6$ alkyl or $C_1$-$C_4$ alkoxy; and
$R_5$ is H.

2. The UV absorber of claim 1 wherein:
$R_1$, $R_2$, and $X_3$=nothing;
$X_1$ is Cl;
$R_3$ is nothing;
$X_2$ is a polymerizable group of formula Ia;
$R_7$ is —(CH$_2$)$_3$—;
$X_4$ is O;
$R_8$ is C=O;
$R_9$ is methyl;
$R_{10}$ is H;
$R_4$ and $R_6$ are t-butyl; and
$R_5$ is H.

3. An ophthalmic device material comprising the UV absorber of claim 1 and a device-forming monomer selected from the group consisting of acrylic monomers and silicone-containing monomers.

4. The ophthalmic device material of claim 3 wherein the ophthalmic device material comprises from 0.1 to 5% (w/w) of the UV absorber of claim 1.

5. The ophthalmic device material of claim 4 wherein the ophthalmic device material comprises from 0.1 to 2% (w/w) of the UV absorber of claim 1.

6. The ophthalmic device material of claim 3 wherein the ophthalmic device material comprises a device-forming monomer of formula [II]:

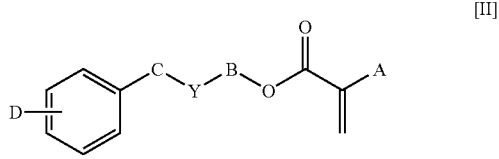

[II]

where in formula [II]:
A is H, CH$_3$, CH$_2$CH$_3$, or CH$_2$OH;
B is (CH$_2$)$_m$ or [O(CH$_2$)$_2$]$_z$;
C is (CH$_2$)$_w$;
m is 2-6;
z is 1-10;
Y is nothing, O, S, or NR', provided that if Y is O, S, or NR', then B is (CH$_2$)$_m$;
R' is H, CH$_3$, C$_n$H$_{2n'+1}$ (n'=1-10), iso -OC$_3$H$_7$, C$_6$H$_5$, or CH$_2$C$_6$H$_5$;
w is 0-6, provided that m+w≦8; and
D is H, C$_1$-C$_4$ alkyl, C$_1$-C$_4$ alkoxy, C$_6$H$_5$, CH$_2$C$_6$H$_5$ or halogen.

7. The ophthalmic device material of claim 6 wherein in formula [II]:
A is H or CH$_3$;
B is (CH$_2$)$_m$;
m is 2-5;
Y is nothing or O;
w is 0-1; and
D is H.

8. The ophthalmic device material of claim 7 wherein the ophthalmic device material comprises a monomer selected from the group consisting of: 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

9. The ophthalmic device material of claim 3 wherein the ophthalmic device material comprises a cross-linking agent.

10. The ophthalmic device material of claim 3 wherein the ophthalmic device material comprises a reactive blue-light absorbing compound.

11. An intraocular lens comprising the UV absorber of claim 1.

12. An intraocular lens comprising the UV absorber of claim 2.

13. An ophthalmic device comprising the ophthalmic device material of claim 3.

14. The ophthalmic device of claim 13 wherein the ophthalmic device is selected from the group consisting of an intraocular lens; a contact lens; a keratoprosthesis; and a corneal inlay or ring.

* * * * *